(12) United States Patent
Liu et al.

(10) Patent No.: US 8,287,471 B2
(45) Date of Patent: Oct. 16, 2012

(54) MEDICAL TREATMENT USING AN ULTRASOUND PHASED ARRAY

(75) Inventors: Hao-li Liu, Taoyuan (TW); Win-li Lin, Taipei County (TW); Hsu Chang, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 817 days.

(21) Appl. No.: 12/033,370

(22) Filed: Feb. 19, 2008

(65) Prior Publication Data

US 2008/0200806 A1    Aug. 21, 2008

Related U.S. Application Data

(60) Provisional application No. 60/890,723, filed on Feb. 20, 2007.

(51) Int. Cl.
*A61N 7/02* (2006.01)

(52) U.S. Cl. ............... 601/3; 601/2; 600/407; 600/411; 600/427; 600/439; 600/444; 600/447; 600/459

(58) Field of Classification Search ............... 601/2, 3; 600/439, 444, 447, 459
See application file for complete search history.

(56) References Cited

U.S. PATENT DOCUMENTS

| | | | | |
|---|---|---|---|---|
| 5,368,032 A | * | 11/1994 | Cline et al. | 600/411 |
| 5,553,618 A | * | 9/1996 | Suzuki et al. | 601/3 |
| 5,859,891 A | * | 1/1999 | Hibbard | 600/427 |
| 5,944,663 A | * | 8/1999 | Kuth et al. | 600/411 |
| 6,042,556 A | * | 3/2000 | Beach et al. | 601/3 |
| 6,613,005 B1 | | 9/2003 | Friedman et al. | |
| 6,618,620 B1 | * | 9/2003 | Freundlich et al. | 601/3 |
| 6,692,450 B1 | | 2/2004 | Coleman | |
| 6,785,572 B2 | | 8/2004 | Yanof et al. | |
| 7,070,327 B2 | * | 7/2006 | Collins | 378/206 |
| 2006/0094988 A1 | * | 5/2006 | Tosaya et al. | 601/2 |

OTHER PUBLICATIONS

McGough et al. "Treatment planning for hyperthermia with ultrasound phased arrays ," Ultrasonics, Ferroelectrics and Frequency Control, IEEE Transactions on , vol. 43, No. 6, pp. 1074-1084, Nov. 1996. doi: 10.1109/58.542051.*
Civale et al. "The Use of a Segmented Transducer for Rib Sparing in HIFU Treatments". Ultrasound in Med. and Biol., vol. 32, No. 11, pp. 1753-1761, 2006.*

* cited by examiner

*Primary Examiner* — Brian Casler
*Assistant Examiner* — Phong K Huynh
(74) *Attorney, Agent, or Firm* — Occhiuti Rohlicek & Tsao LLP

(57) ABSTRACT

A medical system and method for treating a disorder of a subject by thermal ablation, e.g., focused ultrasound thermal ablation, are provided. The method includes obtaining medical images that include at least one image of subject's chest and ribs to reconstruct a three-dimensional chest-rib distribution; and applying ultrasound waves on a target point beyond the subject's ribs by selectively activating one or more elements of an ultrasound phased array to avoid ultrasonic energy absorption or reflection by an intervening rib based on a calculation of a relationship between the three-dimensional chest-rib distribution and an acoustic emission direction.

21 Claims, 5 Drawing Sheets

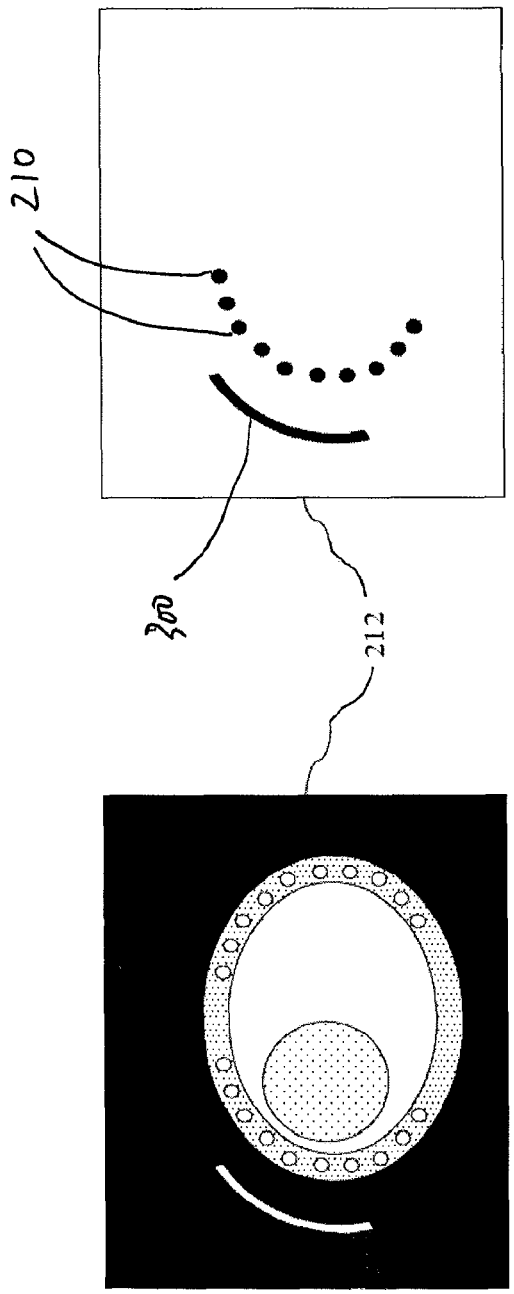
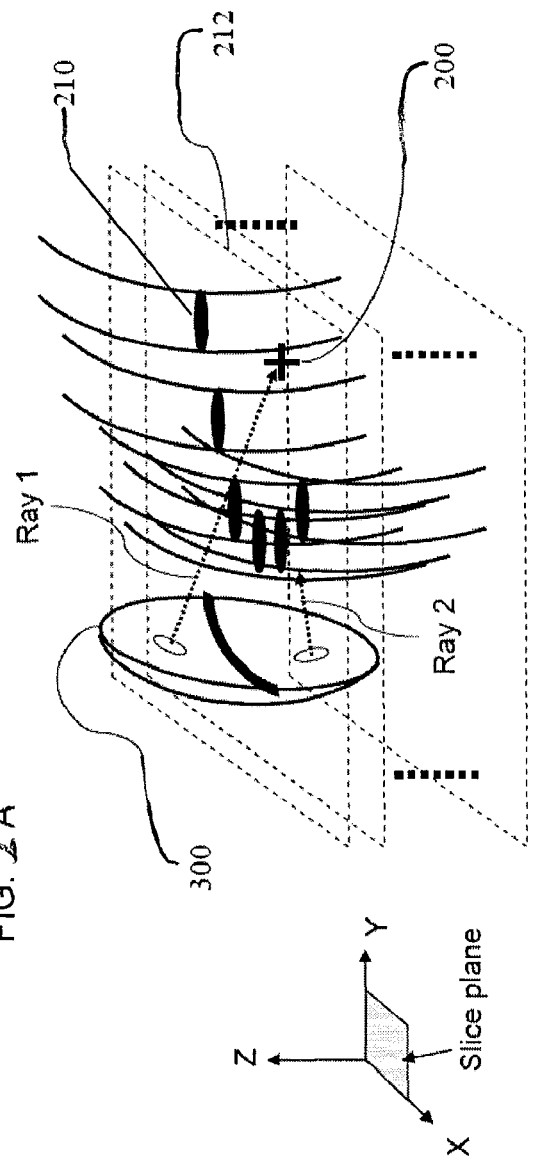
FIG. 2A
FIG. 2B
FIG. 2C

MEDICAL TREATMENT USING AN ULTRASOUND PHASED ARRAY

CROSS REFERENCE

Pursuant to 35 U.S.C. §119(e), this application claims priority to U.S. Provisional Application 60/890,723, filed on Feb. 20, 2007. The contents of the provisional application are incorporated by reference.

BACKGROUND OF THE INVENTION

The invention pertains to medical methods and systems, more particularly, to methods and systems for noninvasively performing a transrib focused ultrasound therapy to treatment areas blocked by the chest ribs.

Focused ultrasound thermal ablation can be used to focus energy onto soft tissues noninvasively and induce a localized temperature elevation (e.g., 30-55° C.) within a few seconds. The resulting high temperature can generate irreversible tissue necrosis at the target region, while not damaging the surrounding normal tissues. Clinical studies have shown the feasibility, safety, and effectiveness of the focused ultrasound treatment modality for treating hepatocellular carcinoma (HCC) and other liver tumors.

BRIEF SUMMARY OF THE INVENTION

In one aspect, in general, a method of thermal ablation (e.g., focused ultrasound thermal ablation) can be used to treat a disorder of a subject. The method includes obtaining medical images that include at least one image of subject's chest and ribs to reconstruct a three-dimensional chest-rib distribution; and applying ultrasound waves on a target point beyond the subject's ribs by selectively activating and/or deactivating one ore more elements of an ultrasound phased array to avoid ultrasonic energy absorption and/or reflection by an intervening rib based on a calculation of a relationship between the three-dimensional chest-rib distribution and an acoustic emission direction.

Aspects can include one or more of the following features.

The method further includes moving the ultrasound phased array proximal to the subject's chest before the applying step.

The medical images comprise at least one member of the group of medical images: Computed tomography (CT), Magnetic resonance imaging (MRI), Positron emission tomography (PET), single-photon emission computed tomography (SPECT), and ultrasonography.

The ultrasound phased array is held by a motor-driven device mounted on a positioning system.

The motor-driven device comprises a robot arm or other types of mechanical positioning system. The robot arm/mechanical positioning system is compatible with a device to obtain the medical images.

The selectively activating and/or deactivating is controlled by an element-activation control unit.

Applying ultrasound waves includes driving one or more elements of the ultrasound phased array by a multiple-channel ultrasound driving system.

The selective activating and/or deactivating ultrasound phased array elements further includes controlling each element of the ultrasound phased array with respective amplitude and relative phase shift independently to focus the ultrasound waves for those elements been activated.

The calculation is repeated while the ultrasound phased array is moving.

The acoustic emission direction is calculated by a ray-tracing algorithm to determine an activation status for each element of the ultrasound phased array.

The ultrasound phased array has an overall concave shape.

Each element of the ultrasound phased array is smaller than a gap of the intercostal muscle between the ribs.

The reconstructing includes detecting at least one of a rib boundary and an ultrasound phased array boundary based on an edge detection algorithm and an auto-segmentation algorithm.

The method further includes marking one or more elements of the ultrasound phased array according to their positions with respect to the three-dimensional chest-rib distribution.

Obtaining medical images includes at least one of: obtaining the medical images manually by an operator, and obtaining the medical images automatically by a treatment planning unit.

In another aspect, in general, a method of focused ultrasound thermal ablation is used on a position in a first group of biological tissues among a second group of biological tissues inside a subject's body. The method includes obtaining medical images that include at least one image of the position to obtain three-dimensional distribution information to show a distribution of the position and the second group biological tissues in three-dimensional coordinates, and applying ultrasound waves on the position beyond an intervening biological tissue of the second group of biological tissues that intervenes a direction of the ultrasound waves by selectively activating and/or deactivating one or more elements of an ultrasound phased array to avoid ultrasonic energy absorption and/or reflection by the intervening biological issue based on a calculation of a relationship between the three- dimensional distribution information and the direction of the ultrasound waves. The method can further include moving the ultrasound phased array proximal to said position before the applying step.

In another aspect, in general, a system for conducting focused ultrasound thermal ablation is used to treat a disorder of a subject, e.g., a transrib abdominal disease. The system includes: an image processing unit for obtaining medical images that include at least one image of subject's chest and ribs, and to reconstruct a three-dimensional chest-rib distribution based on the medical images; an ultrasound phased array having a plurality of elements for producing ultrasound waves; means for moving said ultrasound phased array proximal to the subject; an activator for activating or deactivating each of the plurality of elements of said ultrasound phased array; and a controller for controlling a relative position of said ultrasound phased array and said image processing unit, and for controlling said activator to determine an activation status of each of the plurality of elements of said ultrasound phased array to avoid ultrasonic energy absorption or reflection by an intervening rib based on a calculation of a relationship between said three-dimensional chest-rib distribution and an acoustic emission direction. The unit, the ultrasound phased array, the means for moving, the activator, and the controller are electrically connected.

Aspects can include one or more of the following features.

The image processing unit includes an image scanner to obtain medical images and an image processor to reconstruct a three-dimensional chest-rib distribution. The image processor detects at least one of a rib boundary and an ultrasound phased array boundary based on edge detection algorithm and auto-segmentation.

The image processor further marks at least some ultrasound phased array elements according to their positions with respect to the three-dimensional chest-rib distribution.

The medical images include at least one member of the group of medical images: CT, MRI, PET, SPECT and ultrasonography.

The means for moving comprises a motor-driven device which is mounted on a positioning system.

The motor-driven device comprises a robot arm or other types of mechanical positioning means. The robot arm/mechanical positioning system is compatible with a device to obtain the medical images.

Each of the plurality of elements of the phased array is driven by a multiple-channel ultrasound driving system. The multiple-channel ultrasound driving system is electrically connected between the activator and the controller and is controlled by the controller. The multiple-channel ultrasound driving system is configured to control each of the plurality of elements with respective amplitude and relative phase shift independently to focus the acoustic emission.

The calculation is repeated while the ultrasound phased array is moving.

The acoustic emission direction is calculated by a ray-tracing algorithm to determine the phased activation status for each array element.

The ultrasound phased array has an overall concave shape.

Each element of the ultrasound phased array is smaller than a gap of the intercostal muscle between the ribs.

The controller comprises a monitoring unit to control the position of the phased array and an image scanner and a treatment planning unit to plan a treatment strategy and operation procedure.

Aspects can have one ore more of the following advantages.

Techniques can be used to overcome some complications of focused ultrasound therapy. For example, third-degree skin burns, which are usually associated with the ribs overlying the treatment region, can be mitigated. These ribs can attenuate the transmission of ultrasound energy toward the target area, and also absorb or reflect the incident energy so as to cause skin burns. Moreover, the ribs represent a large inhomogeneity in the medium that can cause phase aberrations, with the resulting focal beam distortions preventing the required temperature increase at the target area. These problems have lead to a requirement for the partial surgical removal of ribs prior to a focused ultrasound ablation session, which significantly degrades the noninvasive nature of focused ultrasound therapy.

By investigating the characteristics of focused ultrasound thermal ablation for liver treatment, a treatment configuration can be found that includes the prevention of skin burns and the avoidance of rib surgery. Using an ultrasound phased array can provide more flexible and dynamic focusing than a spherical single-element transducer. Moreover, the elements of the phased array can be independently activated or turned off. These techniques can increase the possibility of treating the liver tumor through intact ribs.

Another advantage is that techniques described herein can reduce the acoustic energy absorption of ribs and rib damage by deactivating those ultrasound phased array elements that directly emit the ultrasonic energy into the ribs based on the determination of the beam direction and the three-dimensional rib geometry.

Another advantage is that techniques described herein can prevent the accompanying intercostal muscle burn and damage due to the rapid acoustic energy absorption from the ribs.

Another advantage is that techniques described herein can increases the acoustic energy deposition ratio between the target and the ribs, leading to an increased chance to reach the therapeutic acoustic energy level in the target.

Another advantage is that techniques described herein can prevent the partial rib removal procedure that would otherwise be used in order to prevent the acoustic energy from being blocked by the ribs, as well as the rib and intercostal muscle burn damage.

Still further advantages and benefits are that further treatment planning and optimization procedures can be used to increase or maximize the acoustic energy efficiency and to reduce or minimize the total emitted energy to lower possible risks of acoustic energy emission dosage.

"Transrib" as used herein means across, on the other side of, or beyond the ribs of a subject.

Other features and advantages will become apparent from the following description, and from the claims.

BRIEF DESCRIPTION OF THE DRAWINGS

Various components and arrangements of components, and various steps and arrangements of steps can be used. The drawings are only for purposes of illustrating exemplary implementations and are not to be construed as limiting the invention.

FIGS. 2A-2C show an alternative configuration for image processing a series of pre-procedure medical images to identified the coordinates of the ribs and then reconstruct the three-dimensional rib distribution with respective to the ultrasound phased array.

DETAILED DESCRIPTION

Figure 1:
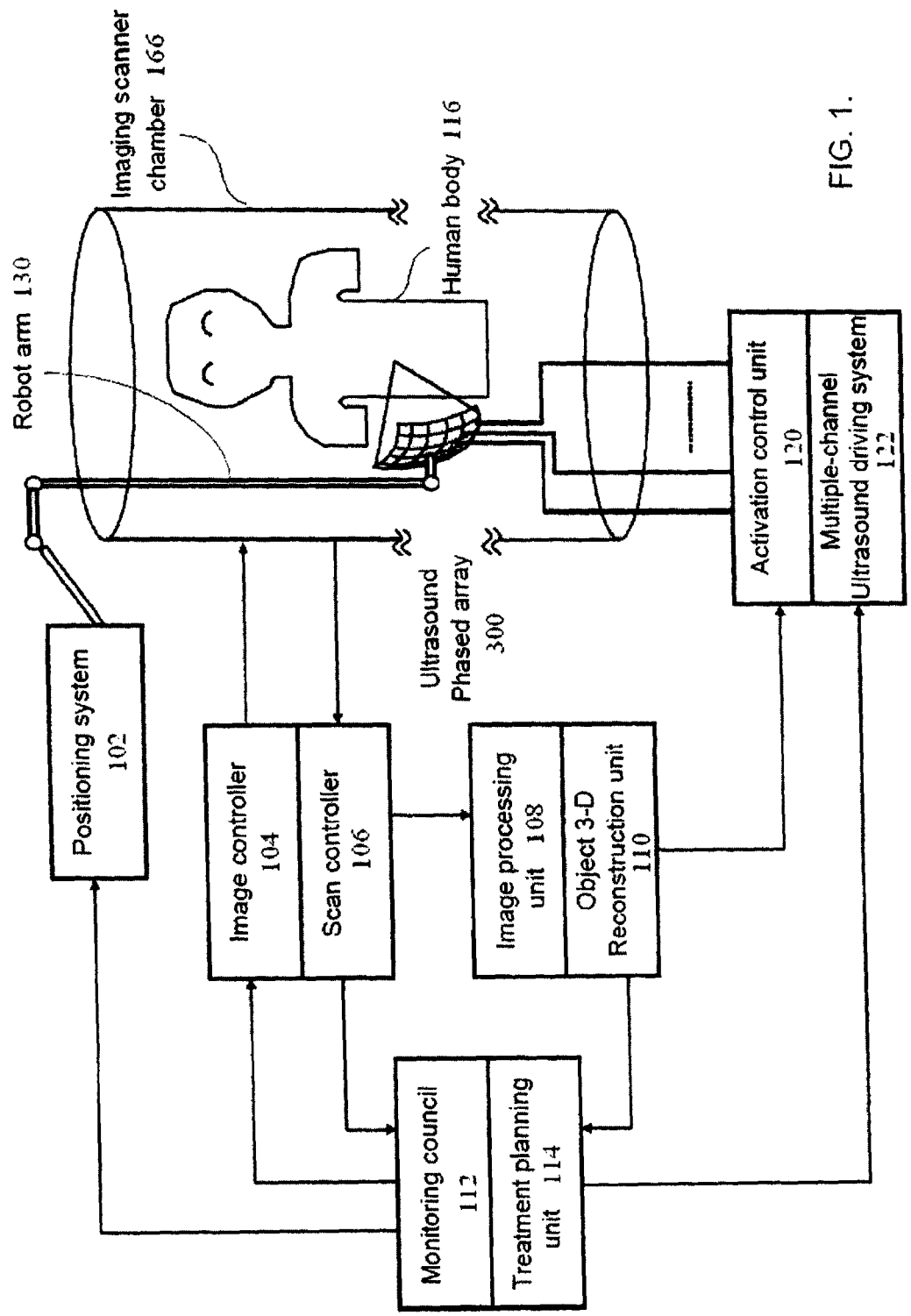
FIG. 1 is diagrammatic illustration of an exemplary image-guided ultrasound phased array interventional medical procedure system.
Figure 3:
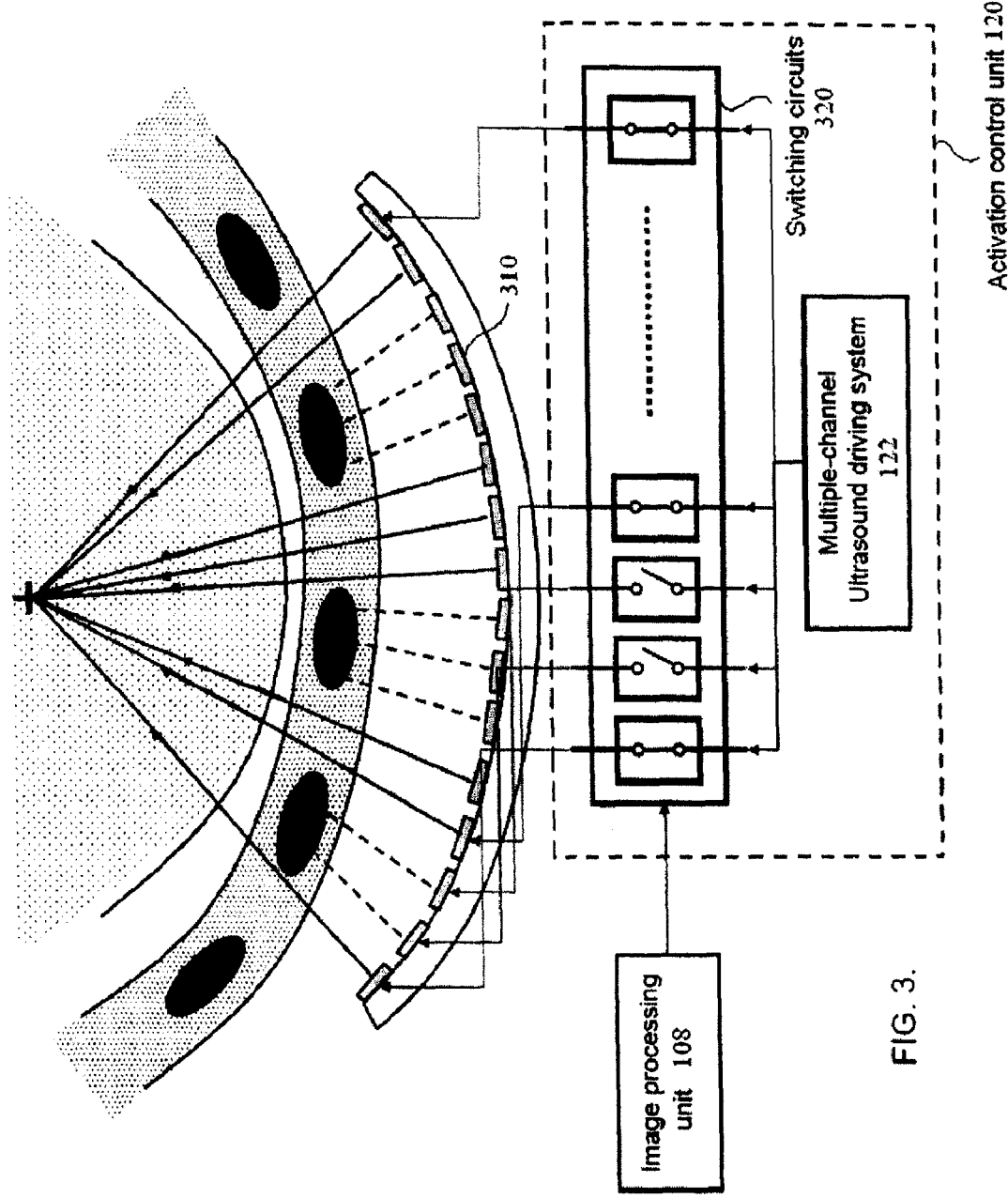
FIG. 3 depicts an electrical control subsystem for independently activating or deactivating the element of the phased array based on the information about the three-dimensional rib distribution and estimation of the incident direction of the ultrasound beam.

FIG. 1 shows an exemplary image-guided interventional medical procedure system for performing a transrib therapeutic procedure using ultrasound phased array 300 of transducer elements 310 (FIG. 3). The system generally includes an ultrasound phased array 300, a robot arm 130 and a positioning system 102 to mechanically position the ultrasound phased array 300 to an accurate coordinate, an imaging controller 104 and scan controller 106 to generate a series of anatomical medical images, a multiple-channel ultrasound driving system 122 to generate radio-frequency signals to drive each transducer element 310, an activation control unit 120 to dynamically activate each of the transducer elements 310, an image processing unit 108 and a 3-D object reconstruction unit 110 to identify the relative 3-D coordinates between the ribs and the ultrasound phased array 300, and a monitoring console 112 and a treatment planning unit 114 for treatment procedure control.

In the illustrated exemplary system, an imaging scanner includes an imaging scanner chamber 166 in which a subject 116 or at least a portion of the subject's body is situated, and can be implemented using any scanner type such as a computed tomography (CT) scanner or a magnetic resonance imaging (MRI) scanner. For example, a subject support such as an operating table, bed or the like, suspends or otherwise can hold the subject 116 received in the chamber 166 of the scanner, such as a human or animal patient, at least partially within the examination region such that the field of view of the produced sliced medical imaging cuts through a region of interest of the subject 116, for example, the chest portion.

A source of ultrasound radiation produced by an ultrasound applicator, in this exemplary system the ultrasound phased array 300, is arranged in the imaging scanner chamber 166 being held by a controllable robot arm 130. The robot arm 130 is controlled by a positioning system 102 outside the imaging scanner chamber 166, which is controlled by the monitoring console 112. In some systems, characteristics of the robot arm 130 can be selected to be compatible with the imaging scanner. For example, if an MRI scanner serves as the imaging scanner, then a component of the robot arm that is inside the imaging scanner chamber 166 should be made of materials that are magnetically compatible (e.g., antimagnetic and non-metal material such as plastic- or glass-made material).

The imaging scanner is controlled by the imaging controller 104 and the scan controller 106 to produce a series of 2-D anatomical images 212 (FIGS. 2A and 2B). Those images are processed by the image processing unit 108 to identify the relative position of the ultrasound phased array 300 and the position of the ribs. Then the 2-D coordinates of the ultrasound phased array 300 and the rib information from the images can be reconstructed to the respective 3-D coordinates by the 3-D object reconstruction unit 110. A ray-tracing algorithm can be used to calculate the acoustic emission direction from each transducer element 310 to the target point 200 (FIG. 2C). The emission directions calculated using the ray-tracing algorithm and other relevant information can be used to determine the optimized phased array element activation status (i.e., activation of deactivation) of each transducer element 310. The activation control unit 120 that includes the multiple-channel ultrasound driving system 122 is connected to each transducer element 310, and can be used to electrically switch the activation status of each transducer element 310. The multiple-channel ultrasound driving system 122 is controlled by a treatment planning unit 114 and the treatment result can be supervised by the monitoring console 112 in a real-time manner.

The transducer elements 310 can be formed of piezoelectric material, for example, such that they emit acoustic energy from the acoustic emission surface when excited by electrical signals from the drive circuitry with the element activation controlled by the activation control unit 120 based on the information from the 3-D rib reconstruction unit 110 using the ray-tracing evaluation algorithm. In some implementations, the transducer elements 310 and/or the acoustic emission surface are substantially planar, although they may alternatively be provided in a concave shape, or any other shape to provide a desired emission pattern.

In one implementation, the ultrasound phased array 300 may have an overall concave or bowl shape, and a substantially hemispherical shape, such that the array 300 generally defines a portion of a sphere. Such a configuration may be appropriate, for example, for treating regions with highly concentrated acoustic energy into deep-seated tissue. The transducer elements 310 can have a round shape or a square shape, for example. Such shapes allow the flexibility of providing substantially isotropic emission from active transducer elements to each of the directions. The size of a transducer element 310 can be smaller than the gap of the intercostal muscle between the chest ribs, for example. The ultrasound phased array 300 can have a diameter between about 5 to about 20 cm, with the radius of curvature between about 8 to about 25 cm, for example. The total number of transducer elements of the phased array 300 can be about 64 or more, for example. The driving frequency of the transducer elements can be between about 28 kHz to about 10 MHz, or between about 100 kHz to about 1 MHz, for example. Higher frequencies may encounter acoustic energy absorption and may not successfully generate a concentrated energy deposition level at the target position beyond the rib surface. Frequencies lower than 100 kHz may encounter poorer energy focusing ability at the target tissue.

The image-guided interventional medical procedure system includes a robotic arm 130 and a positioning system 102, which holds the ultrasound phased array 300 at a desire position. The robotic arm 130 and the positioning system 102 can include, for example, a fully adjustable multi-jointed multi-segmented arm with each joint having varying degrees of freedom. Accordingly, by appropriately arranging the robotic arm 130 and by appropriately positioning the subject 116 and robotic arm 130 relative to one another, the ultrasound phased array 300 can achieve a desired orientation and energy emission angle. The robot arm is a mechanical positioning means and its function can be substituted by other means of mechanical positioning system.

With reference to FIGS. 2A-2C and continuing reference to FIG. 1, the image processing unit 108 acquires a series of diagnostic medical images (e.g., using CT, MRI, PET, SPECT, or ultrasonography) prior to the system conducting the interventional medical procedure. The field of view (FOV) of the images can be selected to cover: (1) the target region surrounding the target point 200 of the subject (e.g., referred to a tumor or partial organ), (2) the ribs 210, which may be situated in an area through which the ultrasonic beams propagate, and (3) the ultrasound phased array 300, as illustrated in FIGS. 2A and 2B. The images can represent slices within a desired plane and the scanning direction for each image slice 212 can be in a coronal (i.e., Y-Z direction in FIG. 2C), saggittal (i.e., X-Z direction in FIG. 2C), or transverse (i.e., X-Y direction in FIG. 2C) direction, for example. For a given image slice 212, image processing methods can be employed to detect the relative spatial coordinates and the regions occupied by the ribs 210 and the ultrasound phased array 300, as illustrated in FIG. 2B. For example, an edge detection algorithm and auto-segmentation algorithm can be employed to detect the boundaries of the ribs 210 and phased array 300. The algorithm can include a function that can identify and label the boundary, for example, a virtual label identifying the "phased array part", the "rib part", and the "target point" 200. The image processing procedures can be employed for each of the acquired images. The image processing unit 108 can process a series of the images in a series manner or a in a parallel manner. The processed imaging data, which may differ from the original raw images, are stored in a memory controlled by the monitoring console 112 for the continuing 3-D object reconstruction process.

As illustrated in FIG. 2C, the 3-D object reconstruction unit 110 can use the processed images containing the identified edge with the referred virtual labeling in numerical algorithms (such as a surface rendering algorithm) to automatically and correctly connect the identical labeled boundary to form a 3-D object distribution. For example, the reconstructed objects can include the ultrasound phased array 300, the target point 200, and the ribs 210 intervening between the target point 200 and the ultrasound phased array 300. As shown, the reconstructed 3-D objects extend through a plurality of image slices 212 including a front image slice, a set of intervening image slices, and a back image slice. Based on information about the positions of the transducer elements 310 of ultrasound phased array 300, the position of the center of each transducer element can be marked and superimposed into the 3-D object coordinate system. Besides the positions of the element centers, the designated target point 200 can also be given to the treatment planning unit 114.

With reference to FIG. 3 and continuing reference to FIG. 2C, the element activation control unit 120 is controlled according to a treatment planning algorithm that commands the multiple-channel ultrasound driving system 122 to dynamically activate the transducer elements 310 of the phased array based on feedback information including the reconstructed 3-D object coordinates. The multiple-channel ultrasound driving system 122 is configured to control transducer elements by applying signals over different channels with respective amplitude and relative phase shift independently to focus the emitted ultrasound waves. Circuitry including switching circuits 320 can be used to control which transducer elements receive the driving signals from the driving system 122.

The treatment planning unit 114 implements a treatment planning algorithm that can control the activation status of each transducer element 310 to reduce or minimize the ultrasonic energy absorption by the intervening chest ribs. For example, a ray-tracing algorithm can be used to achieve this.

One possible exemplary treatment planning algorithm can include the following steps: (1) Ray establishment: The linear trajectories are generated with the center positions of the transducer elements of phased array as the start points and the desired treated target position as an end point. (2) Ray-rib intersecting judgment: It is determined whether the linear trajectories pass through the rendered 3-D rib coordinates. (3) Activation element determination: The activation or deactivation of the transducer elements 310 can be determined based on the information from steps (1) and (2). For example, an element with a respective trajectory passing through the rendered 3-D rib coordinates can be set to be in the "deactivated" status; on the other hand, for elements whose respective trajectory does not intersect any of the rendered 3-D rib coordinates can be set to be the "activated" status.

The activation control unit 120 includes switching circuits 320 that are respectively connected between each of the transducer elements 310 and the multiple-channel ultrasound driving system 122 as illustrated in FIG. 3. The multiple-channel ultrasound driving system 122 includes circuitry to drive the switching circuits 320 with a radio-frequency signal in order to actuate each activated transducer element 310. Additional information regarding driving circuitry that may be appropriate for use with the multiple-channel ultrasound driving system 122 is described in U.S. Pat. No. 5,635,619, which is incorporated herein by reference.

Figure 4:
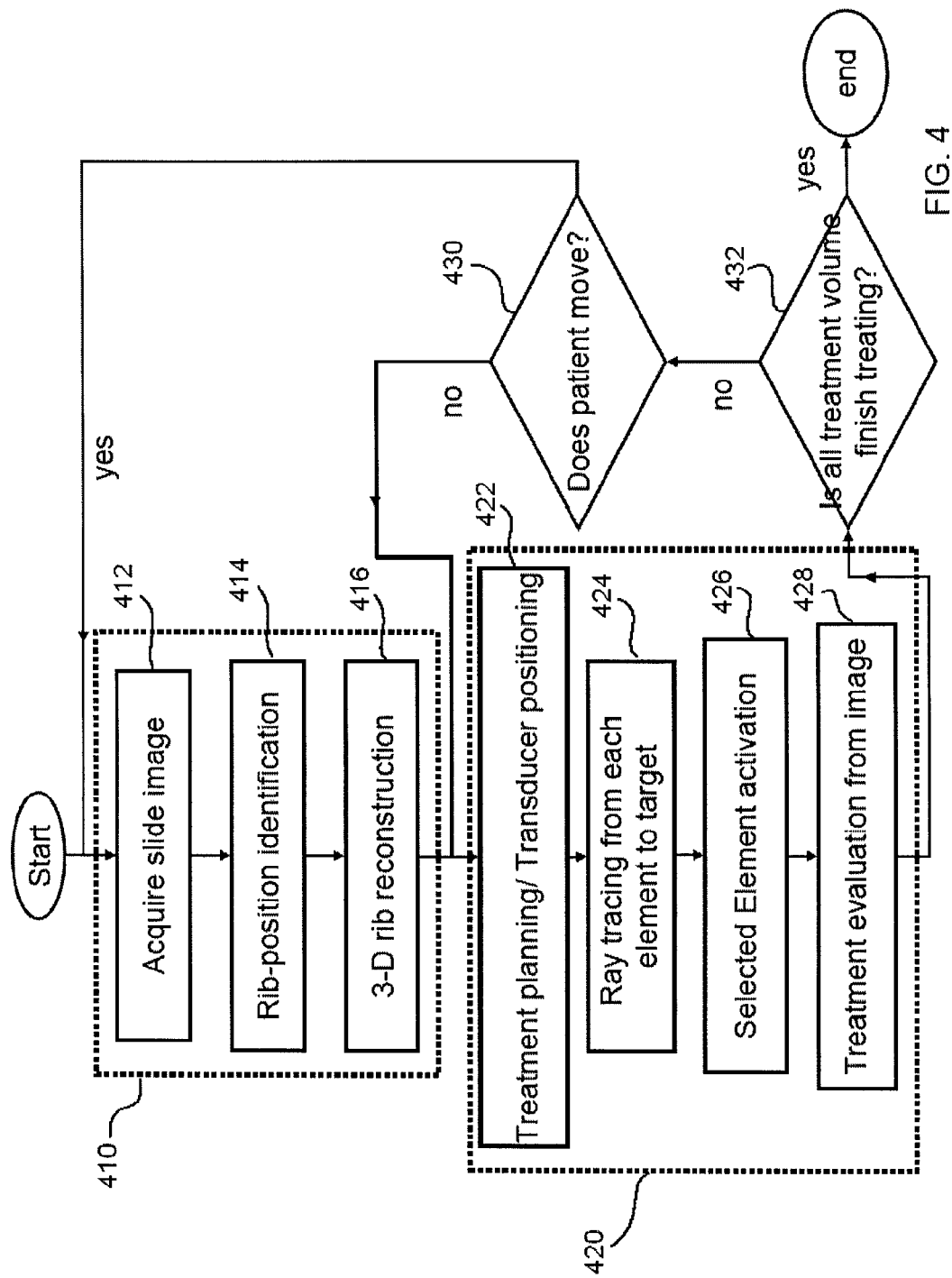
FIG. 4 depicts a flowchart showing the process of applying the system to perform the transrib thermal ablation over a large target volume.

The flowchart shown in FIG. 4 depicts an exemplary process of performing the transrib thermal ablation over a large target volume around a target point. Step 410 in FIG. 4 depicts the process to reconstruct the 3-D rib-target distribution. In sub-step 412, a series of slice-based medical images are obtained by the above mentioned imaging scanner. The region-of-interest of each obtained image is large enough to capture the array of transducer elements, the ribs, and the target region. In sub-step 414, the rib positions are identified and marked through the sliced 2-D medical images either by using automatic or semiautomatic procedures supported by certain imaging processing algorithms. In sub-step 416, the series of post-processing sliced medical images are three-dimensionally reconstructed. More specifically, the 3-D object distribution of ultrasound phased array 300, the rib distribution, and the target point were transformed and displayed for the use of further steps. In the step 410, to increase the image resolution of the 3-D object distribution, some appropriate interpolation algorithms may be employed to estimate spatial relationships of the aforementioned reconstructed objects for both the scanned sliced plane (e.g., X-Y plane in FIG. 2C) and/or the elevation direction (e.g., Z-direction in FIG. 2C). The position of ultrasound phased array 300 can be used as a reference for later steps in the process, and the chest-rib distribution can be assumed to be fixed.

Step 420 shows a portion of the process that employs the ultrasound phased array 300 to perform the therapeutic treatment over a designated volume. The designated volume, particularly, contains a larger volume than the therapeutic area caused by a single sonication (or emission of ultrasound energy) from the ultrasound phased array 300. To target a large volume, multiple sonications can be used in an iterative treatment process. Sub-steps include: (422) treatment planning and transducer orientation adjustment, (424) ray tracing from each phased array element 310 to target, (426) selected element activation, and (428) treatment evaluation from image.

In sub-step 422, a treatment planning algorithm is used to divide the target volume into a number of sub-target regions that can be covered by single ultrasound phased array sonication. In each sonication loop, the algorithm selects a new sub-target region. Then, the robot arm 130 is used to mechanically move the ultrasound phased array 300 to align the target point 200 to the selected sub-target region. The shifting distance of ultrasound phased array 300 can be optimized by the aforementioned treatment planning algorithm which may include wave propagation simulation.

In step 424, the ray-tracing algorithm is used. Based on the new position of the ultrasound phased array 300, the transducer element positions are identified from the reconstructed 3-D phased array distribution. Then, for respective transducer elements 310, the center positions are identified, and the respective normal vectors are calculated, to provide an input of the ray-tracing algorithm. In this step 424, the ray emitted from each respective transducer element 310 is examined to determine whether the ray (from the center of transducer element 310 to the target point 200) collides with the reconstructed chest-ribs. Those transducer elements 310 that have an emitted ray that collides with chest-ribs are marked as a reference for later processing.

In sub-step 426, the transducer elements 310 are selectively connected to the multiple-channel ultrasound driving system 122 by circuitry within the activation control unit 120. The activation control unit 120 determines the transducer element activation status by checking the marked status provided from sub-step 424. For those transducer elements 310 marked in sub-step 424, the activation control unit 120 does not form a connection between that transducer element 310 and the driving system 122 (and thereby deactivates the transducer element). Otherwise, the transducer elements 310 not marked are connected to the driving system 122 to activate the transducer element 310 to deliver the ultrasonic energy.

In sub-step 428, the therapeutic level is evaluated and recorded. For example, an MRI image can be used to provide feedback of the temperature evolution which is then transferred to thermal dosage for therapeutic level evaluation based on some temperature-dependent parameter change. The therapeutic level is recorded in the treatment planning algorithm.

Sub-step 430 and 432 are condition blocks to determine whether all sub-target region treatments are completed and whether realignment of the chest-rib area and/or phased array 300 is necessary. In this example, there are three possible conditional flows as follows:

(i) If all of the sub-target regions were treated and evaluated, the process flow ends;
(ii) If only partial sub-target regions are treated, but the patient doesn't move, treatment of the sub-target region continues to proceed and enters into the process described in sub-step 422.
(iii) If only partial sub-target regions are treated and the patient does move, the chest-rib area and/or the ultrasound phased array 300 can be realigned, and the process flow enters into step 410.

The determination of patient movement can be performed by obtaining and comparing specified image slices between each sub-target region sonication. When patient movement does not occur, two image slices appear to be substantially identical. Otherwise, the two image slices may show differences that can be used to infer movement. Additional information regarding the process to reconstruct the 3-D rib-target distribution and therapeutic level evaluation can be found in Liu et al., *Med. Phys.*, 34(9), 3436.

Figure 5B:
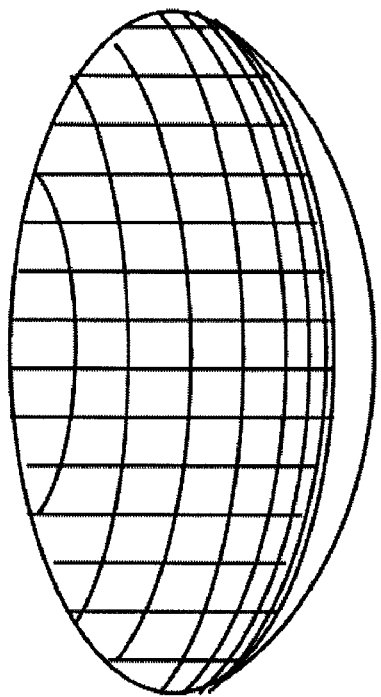
FIGS. 5A-5D depict configurations of an ultrasound phased array.
Figure 5D:
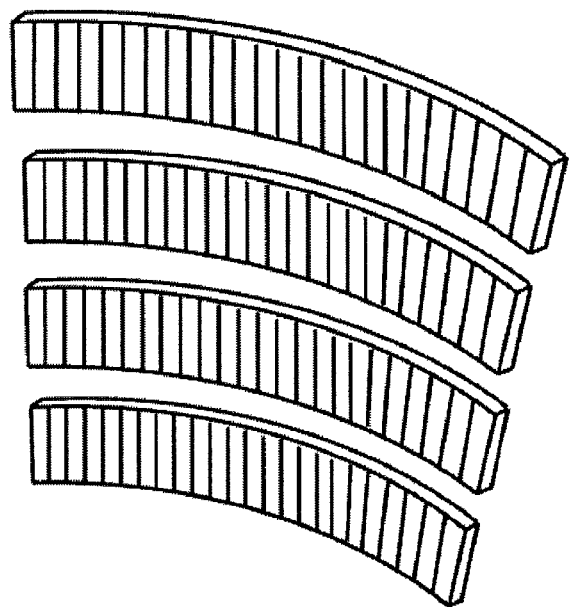
Figure 5A:
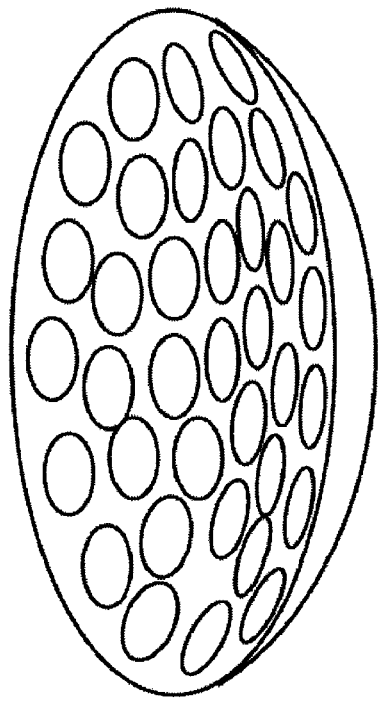
Figure 5C:
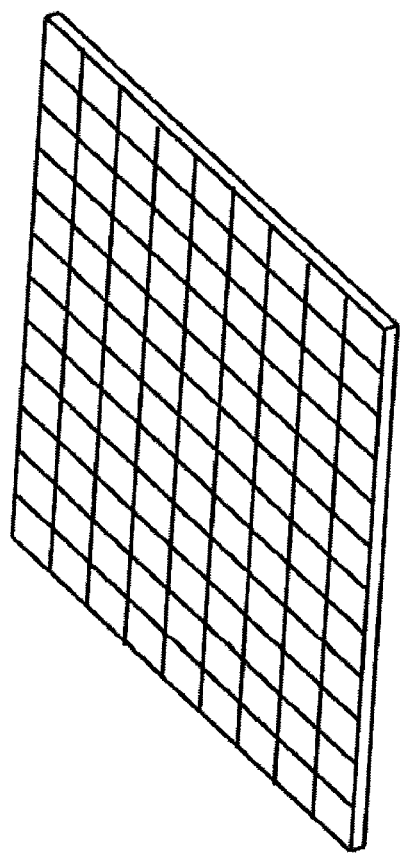

FIGS. 5A-5D show examples of ultrasound phased array configurations which may be used. FIG. 5A illustrates the use of a number of ultrasound transducers on a concave support structure. The transducers may have similar or equal dimension, which may be relatively smaller than the total acoustic emission surface provided by the support structure. In some implementations, the transducers may be arranged on the support structure in a randomized phased array configuration. FIGS. 5B and 5C illustrate the use of support structures with concave or planar surfaces, respectively, and that have a regular and linear dicing of the phased array elements 310. FIG. 5D illustrates the use of a number of 1-D phased arrays with the element dicing direction of each curved support structure along its length. As described above, the acoustic beams generated by each single phased array element 310 within these configurations can be controlled according to the treatment planning algorithm, and independent control of element activation may be used to reduce or eliminate the severe heating and damage of chest ribs.

It will be appreciated that the embodiments described herein are illustrative and that other embodiments, including embodiments incorporating various modifications, can be implemented.

Without further elaboration, it is believed that the above description has adequately enabled the present invention. All of the publications cited herein are hereby incorporated by reference in their entirety.

What is claimed is:

1. A method of treating a disorder of a subject by thermal ablation, said method comprising:
    obtaining medical images that include at least one image of the subject's chest and ribs to reconstruct a three-dimensional chest-rib distribution;
    receiving information representative of results of repeated and real-time calculation of a relationship between the three-dimensional chest-rib distribution and an acoustic emission direction; and
    applying ultrasound waves on a target point beyond the subject's ribs by selectively activating one or more elements of an ultrasound phased array to avoid ultrasonic energy absorption or reflection by an intervening rib based on said repeated and real-time calculation of a relationship between the three-dimensional chest-rib distribution and an acoustic emission direction while there exists relative motion between the ultrasound phased array and the chest-rib distribution;
    wherein obtaining medical images includes detecting at least one of a rib boundary and an ultrasound phased array boundary based on an edge detection algorithm, and an auto-segmentation algorithm,
    wherein said acoustic emission direction is calculated by a ray-tracing algorithm to determine an activation status for each element of said ultrasound phased array, and
    wherein selectively activating includes marking one or more elements of said ultrasound phased array according to their positions with respect to said three-dimensional chest-rib distribution.

2. The method of claim 1, further comprising moving the ultrasound phased array proximal to the subject's chest before said applying step.

3. The method of claim 1, wherein said selectively activating is controlled by an activation control unit.

4. The method of claim 1, wherein said applying ultrasound waves includes driving the one or more elements of said ultrasound phased array by a multiple-channel ultrasound driving system.

5. The method of claim 1, wherein said selectively activating further comprises controlling each of the one or more elements with respective amplitude and relative phase shift independently to focus said ultrasound waves.

6. The method of claim 1, wherein said obtaining medical images include at least one of: obtaining said medical images manually by an operator, and obtaining said medical images automatically by a treatment planning unit.

7. A system for conducting focused ultrasound thermal ablation to treat a trans-rib abdominal disease of a subject, said system comprising:
    an image processing unit configured to obtain medical images that include at least one image of the subject's chest and ribs, and to reconstruct a three-dimensional chest-rib distribution based on said medical images, said image processing unit being configured to detect at least one of: a rib boundary, and an ultrasound phased array boundary based on an edge detection algorithm, and auto-segmentation;
    an ultrasound phased array having a plurality of elements for producing ultrasound waves;
    means for moving said ultrasound phased array proximal to the subject based on a calculation that is repeated while there exists relative motion between the ultrasound phased array and the chest-rib distribution;
    an activator configured to activate or deactivate each of the plurality of elements of said ultrasound phased array based on a calculation of an acoustic emission direction by a ray-tracing algorithm to determine an activation status for each of the plurality of elements; and
    a controller
        configured to control a relative position of said ultrasound phased array and said image processing unit, and
        configured to control said activator to determine an activation status of each of the plurality of elements of said ultrasound phased array to avoid ultrasonic energy absorption or reflection by an intervening rib based on a calculation of a relationship between said three-dimensional chest-rib distribution and an acoustic emission direction;
    wherein said image processing unit, said ultrasound phased array, said means for moving, said activator, and said controller are electrically connected.

8. The system of claim 7, wherein said image processing unit comprises an image scanner to obtain medical images and an image processor to reconstruct a three-dimensional chest-rib distribution.

9. The system of claim 7, wherein said medical images comprise a medical image obtained from an imaging modality selected from the group consisting of: CT, MRI, PET, SPECT, and ultrasonography.

10. The system of claim 7, wherein each of the plurality of elements of said phased array are driven by a multiple-channel ultrasound driving system.

11. The system of claim 10, wherein said multiple-channel ultrasound driving system is electrically connected between said activator and said controller and is controlled by said controller.

12. The system of claim 10, wherein said multiple-channel ultrasound driving system is configured to control each of the plurality of elements with respective amplitude and relative phase shift independently to focus the acoustic emission.

13. The system of claim 7 wherein said controller comprises a monitoring unit to control the position of said phased array and an image scanner and a treatment planning unit to plan a treatment strategy and operation procedure.

14. The method of claim 1, wherein relative motion arises while the phased array is moving.

15. The method of claim 1, wherein said medical images comprise an MRI image.

16. The method of claim 1, wherein said medical images comprise a PET image.

17. The method of claim 1, wherein said medical images comprise a SPECT image.

18. The method of claim 1, wherein said medical images comprise an ultrasonographic image.

19. The method of claim 1, wherein said medical images comprise a CT image.

20. The method of claim 1, wherein applying ultrasound waves on a target point comprises applying ultrasound waves to a tumor in an organ that is partially blocked by at least one rib.

21. The method of claim 20, wherein the organ comprises a liver.

* * * * *